United States Patent [19]
Weyer et al.

[11] Patent Number: 5,387,701
[45] Date of Patent: Feb. 7, 1995

[54] PREPARATION OF 4-HYDROXYMETHYLTETRAHYDROPYRAN

[75] Inventors: Hans-Juergen Weyer, Mannheim; Rolf Fischer, Heidelberg; Werner Schnurr, Herxheim; Norbert Goetz, Worms; Thomas Kuekenhoehner, Boehl-Iggelheim, all of Germany

[73] Assignee: BASF Aktiengesellschaft, Ludwigshafen, Germany

[21] Appl. No.: 130,010

[22] Filed: Sep. 30, 1993

[30] Foreign Application Priority Data

Oct. 5, 1992 [DE] Germany ............... 4233430

[51] Int. Cl.$^6$ ............... C07D 309/06
[52] U.S. Cl. ............... 549/423
[58] Field of Search ............... 549/423

[56] References Cited

U.S. PATENT DOCUMENTS

| | | | |
|---|---|---|---|
| 4,831,166 | 5/1989 | Eckhardt et al. | 549/323 |
| 4,837,346 | 6/1989 | Becker et al. | 549/425 |
| 5,252,755 | 10/1993 | Henkelmann et al. | 549/427 |

OTHER PUBLICATIONS

Journal of the American Chemical Society, vol. 98, No. 20, 29. Sep. 1976, pp. 6350–6353, W. H. Rastetter.
Journal of Organic Chemistry, vol. 32, Jan. 1967, pp. 200–204, W. J. Gensler et al.
Journal of the Chemical Society, Chemical Communications, No. 18,15. Sep. 1976, pp. 734–736, J. E. Baldwin.

Primary Examiner—Nicky Chan
Attorney, Agent, or Firm—John H. Shurtleff

[57] ABSTRACT

A process for preparing 4-hydroxymethyltetrahydropyran comprises reacting tetrahydrofurans of the general formula I

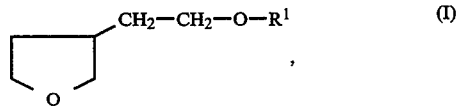

where
R$^1$ is hydrogen, C$_1$- to C$_6$-alkyl or —CO—R$^2$, and
R$^2$ is hydrogen or C$_1$- to C$_6$-alkyl, at from 0° to 400° C. and from 0.001 to 400 bar in the presence of acidic catalysts.

5 Claims, No Drawings

PREPARATION OF 4-HYDROXYMETHYLTETRAHYDROPYRAN

The present invention relates to a novel process for preparing 4-hydroxymethyltetrahydropyran by acid-catalyzed isomerization of 3-(2-hydroxyethyl)tetrahydrofurans.

It is known that 4-hydroxymethyltetrahydropyran can be prepared in three steps: reaction of ethyl acetoacetate with ethylene oxide to form 3-(2-hydroxyethyl)-gamma-butyrolactone (EP-A-246 581), rearrangement to ethyl tetrahydropyran-4-carboxylate (EP-A-284 969), and subsequent catalytic hydrogenation to form 4-hydroxymethyltetrahydropyran (DE-A-4 141 222).

This route to 4-hydroxymethyltetrahydropyran leaves something to be desired on account of the number of reaction steps.

It is an object of the present invention to develop a simpler process for preparing 4-hydroxymethyltetrahydropyran.

We have found that this object is achieved by a novel and improved process for preparing 4-hydroxymethyltetrahydropyran, which comprises reacting tetrahydrofurans of the general formula I

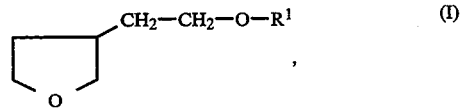

where
$R^1$ is hydrogen, $C_1$- to $C_6$-alkyl or $—CO—R^2$, and
$R^2$ is hydrogen or $C_1$- to $C_6$-alkyl,
at from 0° to 400° C. and from 0.001 to 400 bar in the presence of acidic catalysts.

The process of the invention can be carried out as follows.

The reaction of tetrahydrofurans I to form 4-hydroxymethyltetrahydropyran can in general be carried out at isomerization temperatures of from 0° to 400° C., preferably from 50° to 200° C., particularly preferably from 100° to 150° C., and at pressures of from 0.001 bar to 400 bar, preferably from 0.01 to 3 bar, particularly preferably from 0.05 to 0.5 bar, in the gas or liquid phase, batchwise or preferably continuously in suitable reaction vessels, optionally in an inert solvent.

The substituents $R^1$ and $R^2$ in the compound I have independently of each other the following meanings:
$R^1$, $R^2$
  hydrogen
  $C_1$- to $C_6$-alkyl, preferably $C_1$- to $C_4$-alkyl such as methyl, ethyl, n-propyl, isopropyl, n-butoxy, isobutyl, sec-butyl or tert-butyl, particularly preferably methyl or ethyl,
$R^1$
  acyl $—CO—R^2$.

Suitable tetrahydrofurans I include 3-(2-hydroxyethyl)tetrahydrofuran, whose hydroxyethyl group may be etherified, for example to form the methyl, ethyl, propyl or butyl ether, or esterified, for example with formic acid, acetic acid, propionic acid, butyric acid, n-valeric acid, isovaleric acid or benzoic acid. Particular preference is given to 3-(2-hydroxyethyl)tetrahydrofuran itself.

Suitable acidic catalysts include homogeneous catalysts such as sulfonic acids, e.g. fluorosulfonic acid, chlorosulfonic acid and p-toluenesulfonic acid, halohydric acids, e.g. hydroiodic acid, hydrobromic acid and hydrochloric acid, heteropoly acids, e.g. dodecatungstophosphoric acid, dodecamolybdataphosphoric acid and dodecatungstosilicic acid, carboxylic acids, e.g. trifluoroacetic acid and trichloroacetic acid, mineral acids, e.g. sulfuric acid and perchloroacetic acid, or heterogeneous catalysts such as acid ion exchangers, zeolites or acidic metal oxides in the form of supported catalysts or in compact form. The nature of the carrier material is in general not critical; customary carrier materials such as silica, aluminas, titanium dioxides, activated carbon, silicates or zeolites can be used. If necessary, binders or molding aids can be used for preparing the catalysts. Preference is given to strongly acidic catalysts.

If a heterogeneous catalyst is used, it can be used in the form of a suspension or fixed bed catalyst.

Suitable reaction vessels include reactors such as stirred kettles or tubular reactors. A tubular reactor with a fixed bed catalyst can be operated in upward or downward flow.

Suitable solvents include water, alcohols, ketones, carboxylic acids and esters. If a solvent is present, it should preferably have a higher boiling point than 4-hydroxymethyltetrahydropyran.

Since the thermodynamic equilibrium is distinctly in favor of the tetrahydrofurans I, but 4-hydroxymethyltetrahydropyran has a lower boiling point than, for example, 3-(2-hydroxyethyl)tetrahydrofuran, a particularly preferred embodiment of the process of the invention comprises carrying out the isomerization, for example in a reaction column, with continuous removal of the produced 4-hydroxymethyltetrahydropyran in order that the equilibrium may be shifted until the desired amount of 4-hydroxymethyltetrahydropyran has been obtained.

3-(2-Hydroxyethyl)tetrahydrofuran can be prepared directly and in good yields by hydrogenation of citric acid (NAE 191/92) or citric acid derivatives such as citric esters.

4-Hydroxymethyltetrahydropyran is an intermediate for preparing active compounds/ingredients, for example for crop protection (DE-A-3 121 355).

EXAMPLES 1 TO 15

3-(2-Hydroxyethyl)tetrahydrofuran, obtained by catalytic hydrogenation of triethyl citrate, was rearranged into 4-hydroxymethyltetrahydropyran by heating in the presence of acidic catalysts for 3 h. Each run was carried out with 1 g of 3-(2-hydroxyethyl)tetrahydrofuran.

Table 1 indicates the levels of 4-hydroxymethyltetrahydropyran (4HTP) found in the reactor exit stream under various reaction conditions.

TABLE 1

| Example No. | Catalyst Type | Amount [g] | Temperature [°C] | 4HTP content [mol%] |
|---|---|---|---|---|
| 1 | Fluorosulfonic acid | 0.1 | 100 | 0.4 |
| 2 | Fluorosulfonic acid | 0.1 | 150 | 2.0 |
| 3 | Fluorosulfonic acid | 0.4 | 150 | 5.9 |
| 4 | Sulfuric acid | 0.1 | 100 | 0.5 |
| 5 | Hydroiodic acid | 0.1 | 100 | 0.8 |
| 6 | Trifluoromethanesulfonic acid | 0.1 | 100 | 1.0 |
| 7 | Trifluoromethanesulfonic acid | 0.1 | 150 | 5.1 |
| 8 | Nafion | 0.1 | 150 | 1.9 |
| 9 | Trifluoroacetic acid | 0.1 | 100 | 0.6 |
| 10 | Trifluoroacetic acid | 0.1 | 200 | 4.2 |

TABLE 1-continued

| Example No. | Catalyst Type | Amount [g] | Temperature [°C] | 4HTP content [mol%] |
|---|---|---|---|---|
| 11 | Perchloric acid | 0.1 | 50 | 0.4 |
| 12 | Tungstophosphoric acid | 0.4 | 150 | 3.4 |
| 13 | Tonsil | 0.1 | 150 | 0.3 |
| 14 | Re(3%)/Pd(3%)/C | 0.2 | 200 | 0.4 |
| 15 | ZSM-5 | 0.2 | 200 | 0.8 |

We claim:

1. A process for the preparing 4-hydroxymethyltetrahydropyran which comprises:
reacting 3-(2-hydroxyethyl)tetrahydrofuran at a temperature of from 0° to 400° C. and a pressure of from 0.001 to 400 bar in the presence of an acidic catalyst.

2. A process as claimed in claim 1, wherein the reaction is carried out at from 50° to 200° C. and from 0.01 to 3 bar.

3. A process as claimed in claim 1, wherein the reaction is carried out at from 100° to 150° C. and from 0.05 to 0.5 bar.

4. A process as claimed in claim 1, wherein the reaction is carried out continuously.

5. A process as claimed in claim 1, which is carried out in a reaction vessel with continuous removal of the 4-hydroxymethyltetrahydopyran product from the higher boiling 3-(2-hydroxyethyl)tetrahydrofuran reactant.

* * * * *